(12) United States Patent
Beard et al.

(10) Patent No.: US 7,095,505 B1
(45) Date of Patent: Aug. 22, 2006

(54) OPTICAL INTERFEROMETER SENSOR ARRAY

(75) Inventors: Paul Beard, London (GB); Timothy Noel Mills, London (GB)

(73) Assignee: University College London, London (GB)

( * ) Notice: Subject to any disclaimer, the term of this patent is extended or adjusted under 35 U.S.C. 154(b) by 419 days.

(21) Appl. No.: 10/088,322

(22) PCT Filed: Sep. 14, 2000

(86) PCT No.: PCT/GB00/03534

§ 371 (c)(1),
(2), (4) Date: Jun. 11, 2002

(87) PCT Pub. No.: WO01/20318

PCT Pub. Date: Mar. 22, 2001

(30) Foreign Application Priority Data

Sep. 16, 1999 (GB) .................................. 9921970.1

(51) Int. Cl.
*G01B 9/02* (2006.01)
(52) U.S. Cl. ..................................... 356/502; 356/519
(58) Field of Classification Search ................ 356/502, 356/496, 498, 501, 615, 620, 622, 480, 519, 356/477, 505, 506, 454, 35.5
See application file for complete search history.

(56) References Cited

U.S. PATENT DOCUMENTS

| | | | | |
|---|---|---|---|---|
| 4,034,332 A | * | 7/1977 | Alais | 367/153 |
| 4,360,820 A | | 11/1982 | Forster | |
| 4,399,387 A | * | 8/1983 | Kohji | 310/334 |
| 4,633,715 A | * | 1/1987 | Monchalin | 73/657 |
| 5,125,138 A | * | 6/1992 | Shaw et al. | 29/25.42 |
| 5,812,266 A | * | 9/1998 | Hercher | 356/620 |
| 6,664,006 B1 | * | 12/2003 | Munshi | 429/305 |
| 6,699,717 B1 | * | 3/2004 | Rao et al. | 436/39 |

FOREIGN PATENT DOCUMENTS

| | | |
|---|---|---|
| WO | WO-93/01476 A1 | 1/1993 |
| WO | WO-96/23197 A1 | 8/1996 |
| WO | WO-97/27466 A1 | 7/1997 |

OTHER PUBLICATIONS

Applied Optis, optical Society of America Washngton vol. 35 No. 4, Feb. 1, 1996 pp. 663-675-"Extrinsic optical-Fiber Ultrasound Sensor using a Thin Polymer Film as a Low-Finesse Fabry-Perot Interferometer"-P C Beard et al.
Electronics Letters, IEE Stevenage vol. 33 No. 9, Apr. 24, 1997 pp. 801-803-"Miniature Optical Fibre Ultrasonic Hydrophone using a Fabry-Perot Polymer Film Interferometer"-P C Beard et al.

(Continued)

*Primary Examiner*—Hwa(Andrew) Lee
(74) *Attorney, Agent, or Firm*—Barnes & Thornburg LLP

(57) ABSTRACT

An interferometer sensor has a two-dimensional sensor head (1) comprising a polymer film (4) of substantially uniform thickness. An interrogating signal (12) is provided to the sensor head, the interrogation signal extending across the area of the sensor head and being incident normally to the sensor head (1). An optical sensing device (16) is arranged to receive an optical output signal from the sensor head at a location remote from the sensor head. The sensor converts ultrasound signals appearing over a two dimensional surface to an optical signal pattern, using a polymer interferometer sensing film. Spatial discretisation of the ultrasound signal pattern is performed by an optical sensing device. Such optical devices can be arranged having sufficiently high resolution to enable beam-steering imaging to be performed, including imaging outside the footprint of the sensor head.

14 Claims, 2 Drawing Sheets

OTHER PUBLICATIONS

IUltrasonics, IPC Science and technology Press Ltd, Guildford vol. 37, No. 1, 1999, pp. 45-49-"Fiber-optic multiplayer hydrophone for ultrasonic measurement" Wilkens V et al.

Optics Letters-vol. 24 No. 15, Aug. 1, 1999 pp. 1026-1028-"Optical multiplayer detection array for fast ultrasonic field mapping" V. Wilkens and CH. Koch.

Ultrasonics Sonochemistry, vol. 4, No. 4, Oct. 1, 1997 pp. 273-288-"A strategy for the development and standardisation of measurement methods for high power/cavitaing ultrasonic fields: review of high power field measurement techniques" Hodnett M et al.

* cited by examiner

OPTICAL INTERFEROMETER SENSOR ARRAY

This invention relates to an interferometer sensor, and in particular to an interferometer sensor for detecting an incident acoustic signal pattern over a two-dimensional area, particularly but not exclusively for bio-medical ultrasonic sensing applications.

Time-resolved photoacoustic techniques are well known, which involve the excitation of a sample using sub-ablation threshold laser excitation pulses, the excitation of the sample resulting in the production of ultrasonic thermoelastic waves. The amplitude and temporal characteristics of these waves depend upon the optical, thermal, acoustic and other physical properties of the sample and can be used to provide information relating to its composition and structure.

Various methods have been proposed to enable the analysis of these ultrasonic thermoelastic waves, each using ultrasound detectors arranged on the surface of the sample under analysis. For example, tomographic imaging involves the use of detectors arranged around the periphery of the sample, and a reconstruction algorithm enables a slice image to be generated. To produce a three dimensional image of the sample, a large number of slice images must be obtained. This either requires a large number of discrete detectors positioned over the entire surface of the object, or else repositioning of sensors between each slice image acquisition. Furthermore, the processing required to reconstruct the final three-dimensional image is complex.

Alternatively, a two-dimensional sensor can be employed which spatially resolves the acoustic signal at each point across the surface of the sample, to obtain a volume image.

Line-of-sight sensors rely on the assumption that photoacoustic signals detected at individual sensor elements originate only from sample material along the "line-of-sight" of the sensor element. Of course, if useful penetration depths are required, highly directional sensor elements are required having large aperture, and therefore the lateral resolution is poor. The lateral dimensions of the image are limited to the footprint of the sensor being used as a result of the highly directional sensor elements.

Phase-array sensors rely on small omnidirectional sensor elements and apply synthetic focusing techniques to the image data set to interrogate each point in the irradiated volume. This type of "beam-steering" approach enables signals to be received from subsurface objects that are situated outside the footprint of the sensor.

One difficulty in implementing these methods for bio-medical acoustic imaging applications is the requirement for a high resolution two-dimensional array of acoustic sensors. Conventional sensor elements comprise piezoelectric pressure sensing elements. Difficulties arise in obtaining the required small element size and pitch for unambiguous high-resolution beam-steering with sufficient detection sensitivity.

The article "Optical multilayer detection array for fast ultrasonic field mapping" by V. Wilkens and Ch. Kock in Optics Letters Vol 24, No. 15, 1st Aug. 1999 describes a detection array in which an acoustic signal is detected over a two dimensional area of the surface of the sample under analysis using interferometer principles. The pressure signals appearing at the surface of the sample are converted to optical signals for detection by a remote photodetector or photodetector array. This conversion is performed by an interferometer device comprising a 19 layer dielectric structure deposited over a substrate, to which an interrogation signal is applied. This dielectric structure operates as a pair of mirror surfaces with a small spacing between them. The dielectric layers are relatively hard, having Young's modulus in the range 70 to 100 GPa, and so give poor sensitivity to the incident acoustic signal. To compensate for this, the dielectric structure is arranged to enable the device to operate in a high finesse mode of operation for a relatively narrow bandwidth of signals for detection.

According to a first aspect of the present invention there is provided an interferometer sensor comprising: a two dimensional sensor head comprising a polymer film of substantially uniform thickness disposed over a substrate; an optical interrogation signal source for providing an interrogating signal to the sensor head, the interrogation signal extending across the area of the sensor head and being incident normally to the sensor head, the sensor head providing an optical output signal over the area of the sensor head in dependence on incident signals detected by the sensor; and an optical sensing device arranged to receive the optical output signal from the sensor head at a location remote from the sensor head.

The sensor of the invention converts ultrasound signals appearing over a two dimensional surface to an optical signal pattern, using a polymer interferometer sensing film. Localised variations in the thickness of the sensing film caused by the ultrasound signal pattern being measured modulate the outputs of the sensor head. Spatial discretisation of the ultrasound signal pattern is performed by an optical sensing device. Such optical devices can be arranged having sufficiently high resolution to enable beam-steering imaging to be performed, including imaging outside the footprint of the sensor head. The use of a polymer film interferometer sensor gives rise to high sensitivity and can enable a low finesse mode of operation to be sufficient for image acquisition and processing. Low finesse operation gives improved bandwidth and linearity of response.

Preferably, the optical sensing device comprises a two-dimensional photodetector array. In an alternative example, the photodetecting element comprises a photodiode array of smaller size that the area of the sensor head, arranged to scan the output from the sensor head across its area.

The polymer film preferably has a thickness greater than 5 μm. The thickness is selected to be as large as possible to improve sensitivity, but with the constraint that the thickness should remain below the wavelength of the signal to be detected. For example acoustic signals of 20 MHz in water have an approximate wavelength of 70 μm (taking the speed of sound in fresh water to be 1410 m/s). Accordingly, the polymer sensing film may have a thickness in the range 30 μm to 60 μm.

The polymer film preferably has a Young's modulus less than 15 GPa, to improve the sensitivity of the film to the incident acoustic signal. The polymer film preferably comprises a single layer polymer structure deposited directly onto the substrate.

The interrogation signal source may comprise a continuous wave interrogating laser source. An excitation source may also be provided to supply an excitation signal, for example laser excitation pulses, to a sample for analysis through the sensor head.

The invention also provides a method of manufacturing the interferometer of the invention, comprising the step of forming a polymer sensing film by spin coating a liquid polymer on a transparent substrate. An alternative method comprises thermally evaporating a polymer onto the surface of a transparent substrate; condensing the polymer into a liquid phase; and curing the liquid phase polymer using a radiation source thereby forming a solid polymer film on the substrate. In this case, a radiation source may be used to cure the liquid phase polymer, for example an ultra violet light source or an electron beam, although other curing processes are possible.

These methods each enable deposition of the polymer film directly on to the substrate, and thereby avoid the need for adhesives, which can influence the optical performance of the interferometer. The methods enable simplification of the fabrication process.

Examples of the present invention will now be described in detail with reference to the accompanying drawings, in which.

Figure 1:
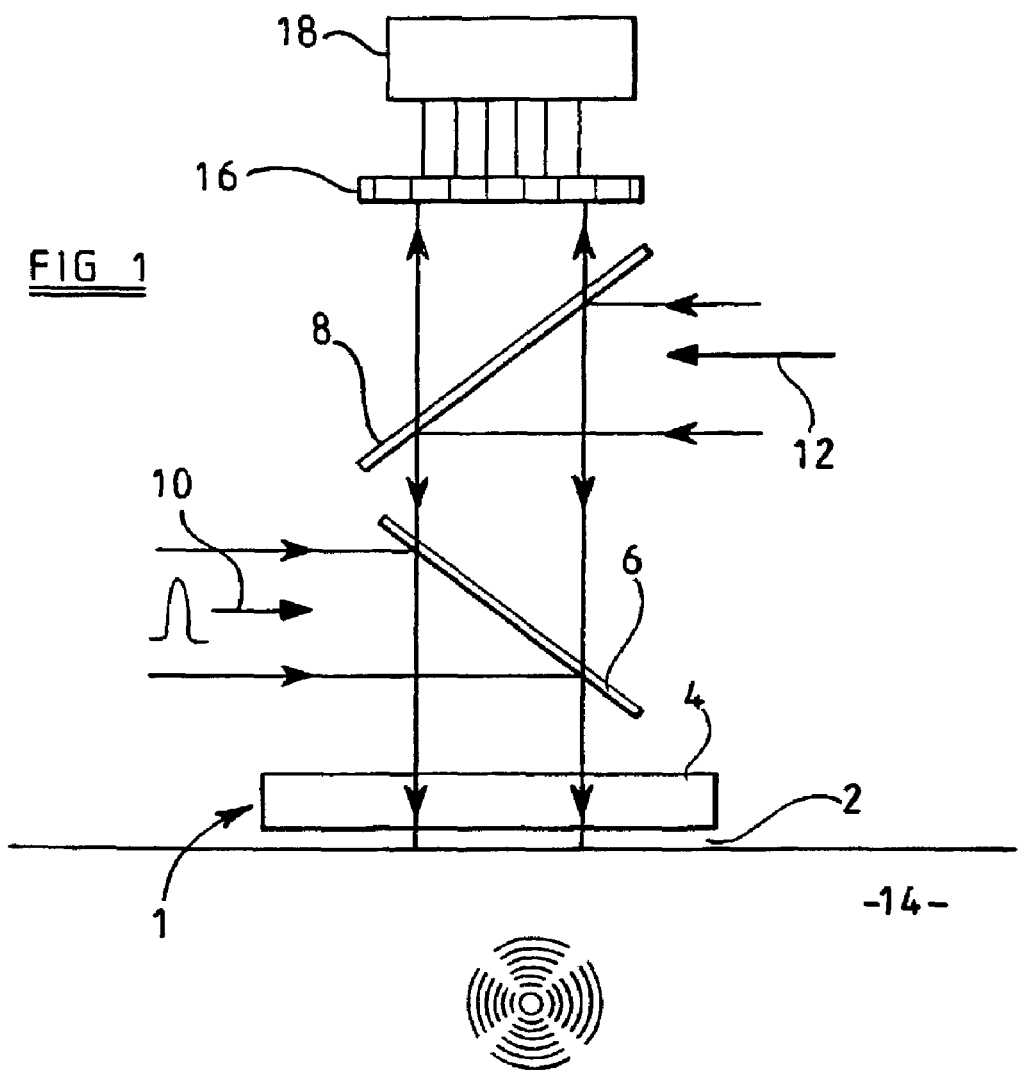
FIG. 1 is a schematic representation of a sensor according to the present invention.

As shown in FIG. 1, the interferometer sensor has a sensor head 1 including a polymer sensing film 2 supported by a transparent substrate 4. The sensor head spans a two dimensional area, and receives a plane wave optical interrogation signal. A modulated reflected output is provided which varies across the area of the signal as a function of localised variations in thickness of the polymer film, which result from incident acoustic signals from the sample under analysis.

First and second beamsplitters 6 and 8 are provided for the supply of signals to and from the sensor head 1. One of the beamsplitters reflects a sample investigation signal from a signal source to the sensor head, and this signal passes through the head 1 into the sample.

The sample investigation signal may comprise laser excitation pulses for irradiating a volume of the sample, to excite the sample to produce ultrasonic thermoelastic waves for detection. In this case, the signal source comprises a pulsed laser source, and the beamsplitter 6 may then comprise a dichroic mirror which reflects the excitation wavelength but which transmits at the wavelength of the interrogation signal (discussed below).

Alternatively, the input signal may comprise an ultrasound signal for ultrasound imaging based on the detection of acoustic echoes at subsurface features where there is an acoustic mismatch. In this case, the signal source may comprise a piezoelectric transducer, and the beamsplitter 6 may then comprise a glass plate which acts as a good acoustic reflector in water and is transparent to the interrogation signal (discussed below). The ultrasound source is then be coupled acoustically to the sensor by having the signal source, beamsplitter 6 and sensor head in water.

The other beamsplitter 8 reflects an interrogation signal from an interrogation signal source to the sensor head 1. A two-dimensional optical sensing device, in the form of a photodiode array 16, is provided at a location remote from the sensor head 1 and receives phase modulated reflected interrogation signals from the sensor head 1. As explained above, since the location of the photodetector array is remote from the sensor head, the spatial discretisation of the acoustic signal is implemented optically at this remote location.

The sensor head comprises a polymer film 2 deposited on to the optically transparent substrate 4 having matched acoustic impedance to minimise acoustic reflections. The acoustic impedance of the polymer layer can also be selected to match the medium in which the sensor is to operate, normally water. The thickness of the film 2 is selected to be as large as possible to improve sensitivity, but with the constraint that the thickness should remain below the wavelength of the signal to be detected. In biomedical photoacoustic imaging techniques, signal frequencies of around 30 MHz are to be detected, having an approximate wavelength of 47 μm. The film thickness should be less than the wavelength of the signal to be detected to achieve sufficient acoustic bandwidth. Thus, the film thickness may be of the order of 40 μm, although the thickness can be selected according to the specific application. The polymer film preferably has a Young's modulus less than 15 GPa, to improve the sensitivity of the film to the incident acoustic signal, and it comprises a single layer polymer structure deposited directly onto the substrate.

In use of the example represented in FIG. 1, which provides laser excitation of the sample, nanosecond excitation laser pulses from a wavelength tuneable source (not shown) are transmitted through the sensor head 1 to the sample 14. The structure of the sensor head is designed to be transparent to the excitation pulses to enable these to pass into the sample. The sensor head 1 is illuminated by the output of a tuneable continuous wave interrogating laser source (not shown) which is arranged to provide interrogation signals 12 to the sample. The polymer sensing film 2 acts as a two-dimensional Fabry Perot interferometer, the mirrors of which are formed at the opposing sides of the polymer film.

The reflections may be obtained simply as a result of the refractive index mismatch at the two sides of the film. Wavelength-selective dielectric reflective coatings or films may be deposited during manufacture of the sensor head 1, designed to be reflective at the wavelength of the continuous wave interrogation signal but transparent to the excitation laser pulses 10 provided by the laser excitation source (not shown), thereby ensuring that the excitation pulses penetrate the sensor head.

The excitation laser pulses cause the generation of photoacoustic waves from each point in the irradiated volume of the sample 14, which are then incident on the polymer sensing film 2. The sample is diffusely irradiated if it is optically scattering, which is the case for biological soft tissue. The incident photoacoustic waves modulate the optical thickness of the polymer sensing film, thereby modulating the reflected interrogation light signals 12. The reflected interrogation light is then directed onto the two-dimensional photodiode array 16 providing a representation of the incident acoustic field across the sensing film 2. In its simplest form, there is a one-to-one mapping so that the effective acoustic element size and spacing corresponds to the optical pixel size and spacing of the optical photodiode array.

The output of the photodiode array 16 is coupled to processor 18 where it is processed to provide a three-dimensional image of the sample 14 being studied, in the same way that the output of a piezoelectric ultrasound detecting array is processed to implement line-of-sight or phased array processing.

To perform line-of-sight imaging, the output of groups of the photodiodes in the array 16 are summed to synthesise an array of directional detector elements that receive photoacoustic signals only along their line-of-sight. For example, photodiode elements having 100 μm pitch may be grouped together to form highly directional elements with an effective diameter of 1 mm.

Phased array processing can also be performed by applying suitable time delays to each element individually to synthetically adjust the receive focus of the array 16. By steering the synthetic receive focus of the phased array through the irradiated volume of the sample 14, a three-dimensional image of the sample 14 can be constructed from a detected data set from a single shot laser excitation pulse. Furthermore, using phased array beam-steering methods, it is possible to obtain an image of the sample outside the footprint of the sensor head.

The phased array approach requires each element to be omnidirectional, and therefore the effective diameter of each element must be small in comparison to the acoustic wavelength. Input signals entering the sensor at an angle to the longitudinal axis will be integrated over the effective area of the sensor, and as a result a smaller effective area improves the directional response of the sensor. Sensor element sizes of a few tens of microns may be desired, which, for one-to-one mapping of the acoustic signal to the photodiode array, requires the pixel diameter of the photodiode pixels of the array to have corresponding size. This may increase the cost of the optical sensor or render it impractical.

Figure 2:
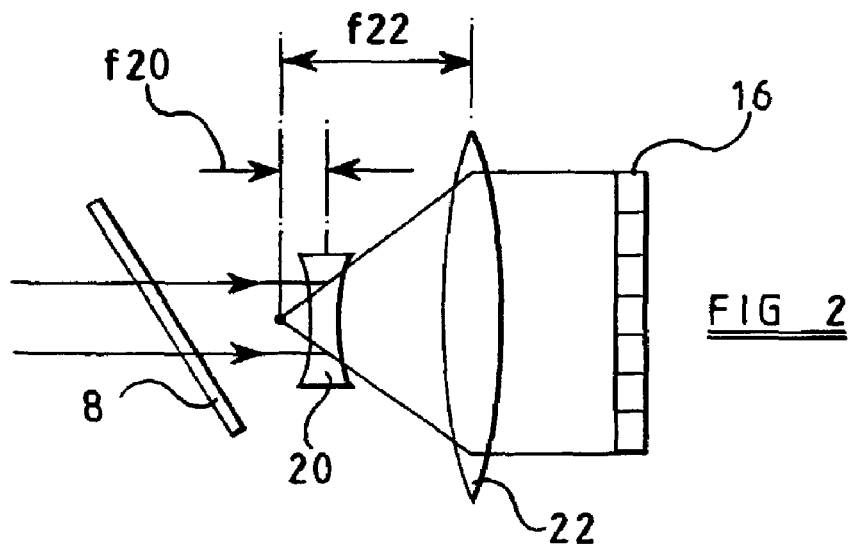
FIG. 2 shows an expanding beam lens arrangement for improving the resolution of the sensor.

To overcome this problem, an optical expanding beam arrangement may be disposed between the sensor head 1 and the array 16, particularly between the beamsplitter 8 and the array 16. As represented in FIG. 2, the expanding beam arrangement may comprise a diverging lens 20 and a converging lens 22 in series. The diverging lens 20 is provided in the path of the light from the beamsplitter 8, and the converging lens is provided closer to the array 16. The focal lengths $f_{20}$, $f_{22}$ of the two lenses are selected so that the focal points coincide, as shown. This ensures that normally incident beams remain normal at the output of the diverging arrangement. The mapping is then no longer one-to-one and the effective acoustic element size and spacing can be reduced. There is a limit to the smallest area of the polymer film that can be addressed due to acoustic cross coupling effects, but it has been found that effective areas of less than 50 μm can be achieved.

The wavelength of the excitation pulses can be selected to obtain desired depth, range and contrast characteristics for the specific application of the sensor. For example, near infra-red wavelengths may penetrate deeply into a sample, whereas improved resolution may be obtained at lower depths with different excitation pulses. The maximum depth at which photoacoustic signals can be detected is an important parameter for the practical use of the sensor in biomedical imaging.

The sensor may operate as a low finesse Fabry-Perot interferometer, and the low Young's modulus gives rise to sufficient sensitivity of the sensor. High finesse operation can also be achieved through the use of low absorption high reflectivity dielectric coatings, which are transmissive at the excitation wavelength. The dynamic range suffers when high finesse operation is achieved, but to increase the upper detection limit the degree of collimation of the interrogation signal can reduced to increase phase dispersion within the interferometer and reduce the finesse.

Figure 3:
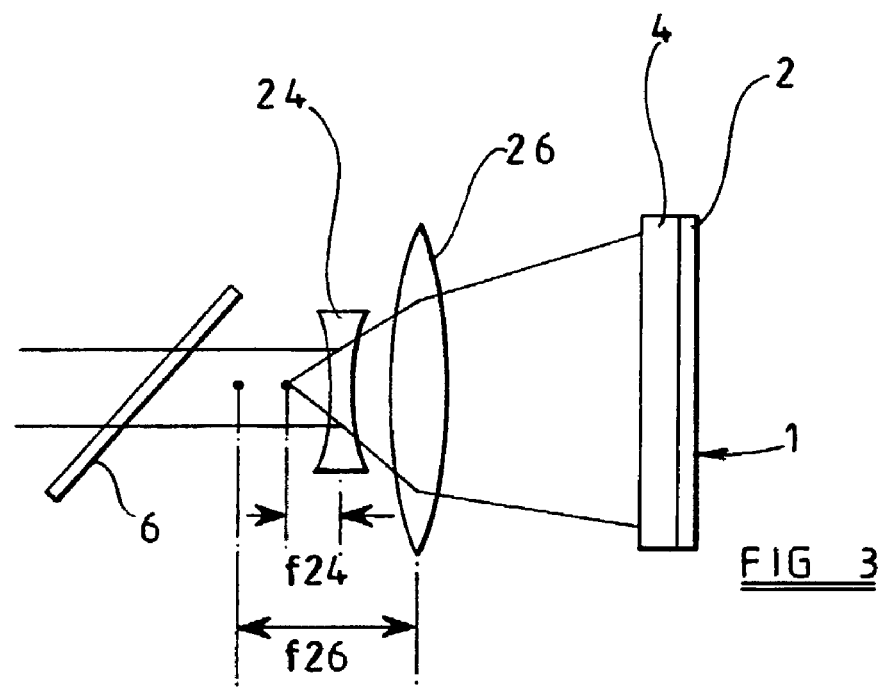
FIG. 3 shows a diverging beam lens arrangement for varying the finesse of the sensor.

This slight reduction in finesse can be achieved by increasing the divergence of the interrogating beam incident on the sensor head. An optically diverging lens arrangement may be provided for this purpose between the beamsplitter 6 and the sensor head 4, as shown in FIG. 3. This arrangement may comprise a diverging lens 24 and a converging lens 26 in series. The diverging lens 24 is provided in the path of the interrogation signal from the beamsplitter 6, and the converging lens is provided closer to the sensor head 1. The focal lengths $f_{24}$, $f_{26}$ and separation of the two lenses are selected so that normally incident beams are caused to diverge. The degree of collimation can then be adjusted by varying the spacing between the two lenses.

The sensor of the invention may be used as a hand held imaging head for use in, amongst other applications, breast cancer detection. In such a device, optical fibre transportation of the interrogation and reflected signals may be employed.

The device may also be used for photo thermal imaging. In addition to detecting ultrasonic photoacoustic signals generated throughout the irradiated volume, the decay of the surface temperature distribution immediately following the absorption of the laser pulse could be detected. This can provide information on the optical and thermal properties of the target. A possible application would be to study the photo thermal response of skin to diagnose abnormalities such as malignant melanoma.

The Fabry Perot sensing film must have good optical and physical properties to enable detection with high signal to noise ratio of the modulation of the sensor film thickness caused by the incident photoacoustic signals. Two possible examples of methods of manufacturing the polymer sensor film described below are spin-coating and polymer deposition from a gas phase via a liquid phase.

To form the polymer sensing film by spin coating, a liquid polymer such as polymethyl methacrylate (PMMA), polystyrene or polyimide, is poured onto a substrate, the substrate then being rotated on a turntable. The liquid polymer is generally obtained by dissolving in an appropriate solvent, which evaporates to leave the polymer. The centripetal forces experienced by the liquid polymer cause it to spread over a central region of the substrate thereby forming the sensor film.

To form the polymer sensing film by polymer deposition from a gas-phase (via a liquid-phase), a bulk sample of the polymer to be used is heated and thermally evaporated onto the substrate using, for example, an electric heater. The vapour then condenses to a liquid on the substrate and is cured using ultra-violet light or an electron beam. This method produces large area Fabry Perot sensing films having good uniformity, which are therefore particularly suitable for bio-medical applications.

PMMA or PTFE are examples of suitable polymers for the formation of the film by thermal evaporation.

Other possible processes for forming the polymer film are sputtering or the parylene polymerisation process.

Even with highly uniform conformal polymer coatings, the optical thickness of the interferometer will vary across the illuminated region of the polymer sensing film. These variations may, for example, be of the order of hundreds of nanometers. These may be large enough to produce significant variations in phase bias and hence sensitivity across the film.

It may therefore be necessary to adjust of control the phase bias so that each point across the sensing area can be interrogated with maximum sensitivity.

The phase bias Φ is given by:

$$\phi = \frac{4\pi nl}{\lambda}\cos\theta$$

where n is the refractive index of the polymer film, l the thickness, λ the light source wavelength and θ is the angle of incidence.

One approach for controlling the phase bias is to vary the interrogation signal wavelength for different points on the film, for example by using a tuneable laser source. A computer controlled tuneable external cavity laser diode and a mechanically scanned photodiode can be used to obtain a map of the reflected fringes over the surface of the sensor to evaluate the variation in optical thickness. The interrogation requirements in terms of speed and wavelength can then be determined for each point one the array.

Figure 4:
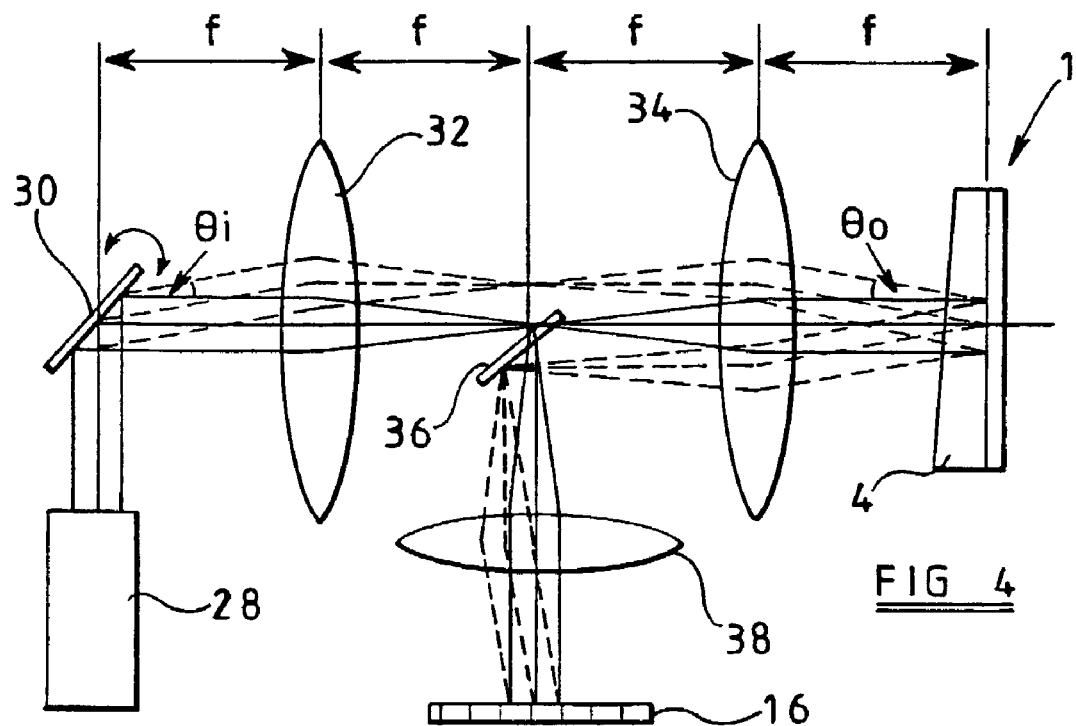
FIG. 4 shows an arrangement for tuning the phase bias of the film.

An alternative is to vary θ which is referred to as angle tuning. FIG. 4 shows one possible implementation of an angle tuning system. Changing the angle $\theta_i$ of the input beam from the laser source 28 using an angle tuning element 30 produces a corresponding change in the angle $\theta_o$ of the light incident on the sensor without translation across its surface. This is achieved by means of the lenses 32, 34 which are spaced by twice their focal lengths, f. The reflected signal from the polymer film 4 is directed by the beam splitter 36 on to the photodiode array 16. The beam splitter 36 is positioned at the focal points of the two lenses 32,34, and directs the signal to the array 16 through a focusing lens 38. This lens and splitter arrangement is configured such that the light reflected from the sensor 1 is imaged on to the photodiode array 16 also without translation as θ is varied.

Using this system, the reflected interference fringes, the spatial derivatives of which can be thought of as contours of uniform sensitivity, can be scanned across the illuminated area of the polymer sensor film enabling each point to be interrogated with optimum sensitivity. The three lenses 32, 34, 38 are of the same focal lengths $f$ and aperture which gives a linear magnification (ratio of output to input beam diameters) and angular tuning gain ($\theta_o/\theta_i$) of unity. If required, various other combinations of lenses could be chosen to increase $\theta_o/\theta_i$ and alter the output beam diameter. The angle tuning element 30 could be an electromechanical device such as a moving coil or moving magnet optical scanning mirror, a rotating polygon mirror or an electro-optic device such as a Bragg cell.

There are various control schemes which enable near-uniform optimum sensitivity to be obtained at each point across the sensing region, namely the area of the illuminating beam.

A closed loop scheme can be employed whereby the output of a single element of the detector array is monitored as $\theta_o$ is varied over a sufficiently large range that a phase shift of at least π radians is produced. The transfer function of the interferometer is thus obtained for that point. The angle that corresponds to the phase bias that results in the maximum sensitivity (i.e. when the phase derivative of the interferometer transfer function is at maximum) is identified and is then used to bias the interferometer. A measurement of the signal is taken and the process repeated in turn for each element of the optical detector array. This approach requires the signal to be detected to be repetitive. To obtain the interferometer transfer function derivative directly and in real time, a small dither angle modulation could be superimposed and continuously monitored.

A continuous scanning approach, by which the sensor is scanned with all angles for each measurement, also assumes that the signal to be detected is repetitive. $\theta_o$ is varied continuously with a sinusoidal or a sawtooth waveform at frequency $f_t$. Providing the resulting interferometer phase bias excursion is at least π radians, all points across the sensing area would at some time within the scan period ($1/f_t$) experience the optimum phase bias corresponding to the maximum sensitivity. Providing the signal repetition rate $f_r$ of the signal to be detected is substantially greater than $f_t$, a signal from any detector element will be detected with optimum sensitivity at least once within the scan period. In practice, the signal would be extracted using envelope detection methods or averaging the absolute amplitude of all the signals obtained over a π phase bias excursion. Additionally, it would be useful to apply a small dither angle modulation at a frequency $f_m$ such that $f_s \gg f_m \gg f_t$ where $f_s$ is the minimum frequency component of the signal. By subjecting the sensor output at the dither frequency to the same processing (averaging or envelope detection) as the signal, variations in interferometer sensitivity across the sensing region, perhaps due to non uniformities in the spatial distribution of the illuminating beam or imperfections in the polymer film or reflective coatings, could be obtained in real time.

In an amplitude modulation scheme, the phase bias is modulated through π radians at a frequency $f_t$ substantially greater than the maximum frequency component of the signal. The output of each detector element is therefore an amplitude modulated carrier which can then be demodulated using conventional AM demodulation techniques. The signal does not need to be repetitive as the interferometer transfer function is effectively sampled many times over the duration of the signal at each point across the sensing region. Since the frequency content of the signal can extend to several tens of MHz if detecting ultrasound fields, the angle tuning element 30 would have to be an electro-optic rather than electromechanical device.

Various modifications will be apparent to those skilled in the art.

The invention claimed is:

1. An interferometer sensor comprising:
   a two-dimensional sensor head comprising a polymer film of substantially uniform thickness disposed over a substrate;
   an interrogation signal source for providing an interrogating signal to the sensor head, the interrogation signal extending across the area of the sensor head and being incident normally to the sensor head, the sensor head providing an optical output signal over the area of the sensor head in dependence on incident signals detected by the sensor; and
   an optical sensing device arranged to receive the optical output signal from the sensor head at a location remote from the sensor head;
   further comprising an optical excitations source arranged to transmit optical excitation pulses through the sensor head into the sample.

2. An interferometer according to claim 1, in which the optical sensing device comprises a two-dimensional photodetector array.

3. An interferometer according to claim 1, in which the optical sensing device comprises a photodiode arranged to scan the output from the sensor head across its area.

4. An interferometer as claimed in any claim 1, wherein the polymer film has a thickness greater than 5 μm.

5. An interferometer as claimed in claim 4, in which the polymer sensing film has a thickness in the range 30 μm to 60 μm.

6. An interferometer as claimed in claim 1, wherein the polymer film has a Young's modulus less than 15 GPa.

7. An interferometer as claimed in claim 1, wherein the polymer film comprises a single layer polymer structure deposited directly onto the substrate.

8. An interferometer as claimed in claim 1, wherein the interrogation signal source comprises a continuous wave interrogating laser source.

9. An interferometer according to claim 1, in which the excitation source comprises a laser light source arranged to provide excitation pulses to the sensor head.

10. An interferometer as claimed in claim 1, further comprising an optical expanding beam arrangement disposed between the sensor head and the optical sensing device.

11. An interferometer as claimed in claim 1, further comprising an optically diverging lens arrangement disposed between the interrogation signal source and the sensor head, for altering the degree of collimation of the interrogation signal provided to the sensor head.

12. An interferometer as claimed in claim 1, further comprising means for measuring the surface temperature at the sensor head.

13. An interferometer as claimed in claim 1, further comprising an optical arrangement for altering the angle of incidence of the interrogation signal on the sensor head.

14. An interferometer as claimed in claim 13, wherein different angles of incidence are selected for different locations of the sensor head.

* * * * *